United States Patent [19]

Adamski et al.

[11] Patent Number: 5,306,733
[45] Date of Patent: Apr. 26, 1994

[54] LOW DENSITY POROUS CROSSLINKED POLYMERIC MATERIALS

[75] Inventors: Robert P. Adamski, Missouri City; Maryanne Mores, Houston; Pui K. Wong, Houston; Diana D. Davis, Houston, all of Tex.

[73] Assignee: Shell Oil Company, Houston, Tex.

[21] Appl. No.: 114,557

[22] Filed: Aug. 30, 1993

[51] Int. Cl.$^5$ .............................. C08J 9/26; C08J 9/28
[52] U.S. Cl. ........................ 521/63; 521/61; 521/64; 521/146; 521/149; 521/150; 524/801; 524/804
[58] Field of Search ............... 521/64, 61, 63, 146, 521/149, 150; 524/801, 804

[56] References Cited

U.S. PATENT DOCUMENTS

| | | | |
|---|---|---|---|
| 3,992,333 | 11/1976 | Emmons et al. | 260/2.5 |
| 4,522,953 | 5/1987 | Barby et al. | 521/64 |
| 4,668,709 | 5/1987 | Jones et al. | 521/146 |
| 4,683,274 | 7/1987 | Nakamura et al. | 526/216 |
| 4,788,225 | 11/1988 | Edwards et al. | 521/147 |
| 5,037,859 | 8/1991 | Williams et al. | 521/55 |
| 5,147,345 | 9/1992 | Young et al. | 604/378 |
| 5,149,720 | 9/1992 | DesMarais et al. | 521/63 |
| 5,189,070 | 2/1993 | Brownscombe et al. | 521/64 |
| 5,200,433 | 4/1993 | Beshouri | 521/64 |
| 5,210,104 | 5/1993 | Bass | 521/64 |

FOREIGN PATENT DOCUMENTS 4-016194A 1/1992 Japan.

OTHER PUBLICATIONS

Crodata Inc, New York, N.Y., Advantages of Sucrose Esters In Formulating Cosmetic Creams And Lotions, *Cosmetics & Toiletries,* vol. 95, No. 3, pp. 70–73, Mar. 1980.

Crodesta Sucrose Fatty Acid Ester, *Crodata:* Nov. 26, 1980, pp. 1–7.

*Primary Examiner*—Morton Foelak

[57] ABSTRACT

Stable high internal phase water-in-oil emulsions containing polymerizable vinyl monomers, crosslinking monomers and polymerization initiators are obtained by using saccharide fatty acid esters as surfactants. The amount of surfactants necessary to form stable high internal phase water-in-oil emulsions is decreased by using saccharide fatty acid esters as surfactants. Further, hydrophobic foams can be obtained by using saccharide fatty acid esters.

13 Claims, No Drawings

LOW DENSITY POROUS CROSSLINKED POLYMERIC MATERIALS

FIELD OF INVENTION

This invention relates to low density, porous, crosslinked, polymeric materials. In one aspect, the invention relates to improved surfactant systems for a high internal phase emulsion polymerization process to manufacture low density porous crosslinked polymeric materials.

BACKGROUND OF THE INVENTION

Polymeric foams can be generally classified as either closed-cell foams or as open-cell foams. Open-cell foams can be used as a matrix to contain various liquids. They are capable of various industrial applications such as, for example, use in wipes and diapers, as carriers and ion exchange resins. For some of these applications, it is desirable to have porous crosslinked polymer blocks which have a very low density and a high capacity of absorbing and retaining liquids. Such high absorption capacity, low density, porous polymer blocks can be prepared by polymerizing a specific type of water-in-oil emulsion known as high internal phase emulsion (HIPE) having relatively small amounts of a continuous oil phase and relatively greater amounts of an internal water phase.

Such high absorption capacity, low density foams are prepared in U.S. Pat. No. 4,522,953 by polymerizing and crosslinking the monomers in the continuous oil phase of a high internal phase water-in-oil emulsion with a polymerization initiator such as potassium persulfate. Generally, these high internal phase water-in-oil emulsions contain at least 90 weight percent of an aqueous liquid as the internal phase. In order to obtain this high internal phase water-in-oil emulsion, a surfactant must be used to stabilize the emulsion.

One class of surfactants used to produce hydrophilic foams by such processes are sorbitan fatty acid esters. Commercial sorbitan fatty acid esters are a combination of mono-, di-, tri-, and tetra-fatty acid esters of sorbitan $C_6(H_2O)_5H_2$, as well as mono- and di-fatty acid esters of isosorbide $C_6(H_2O)_4H_2$ and polyol impurities.

Relatively large amounts of sorbitan fatty acid ester surfactants are required to prepare high internal phase emulsions. To stabilize an emulsion consisting of 30 parts aqueous phase dispersed in 1 part oil phase (by volume), a 10 percent by weight or greater concentration of sorbitan fatty acid ester surfactant in the oil phase is generally needed. Use of such a large amount of surfactant is undesirable since it can adversely affect foam performance by diluting the oil phase. The large quantity of surfactant also increases the raw material cost of producing a foam.

Another disadvantage of using commercially available sorbitan fatty acid esters as the emulsifier is that a watersoluble sludge forms when these surfactants are dissolved in the oil phase. It has been found that polyols such as free sorbitan and isosorbide are the main components of the sludge. The sludge must be removed before the surfactant-oil solution can be used to prepare an emulsion in order to prevent plugging of the process mixing equipment.

It is therefore an object of the present invention to provide a more effective surfactant for the preparation of curable high internal phase water-in-oil emulsions for producing low density crosslinked polymeric materials.

SUMMARY OF THE INVENTION

According to the invention, a process for the production of a porous crosslinked polymeric material is provided, comprising the steps of:

(a) providing a water-in-oil emulsion comprising (i) a mixture of polymerizable monomers comprising at least one vinyl monomer and from about 2 to about 70 weight percent, based on the mixture, of at least one multifunctional unsaturated crosslinking monomer, (ii) at least 90 weight percent, based on the emulsion, of water as the internal phase, (iii) a surfactant comprising at least one saccharide fatty acid ester, and (iv) a polymerization initiator; and (b) heating the water-in-oil emulsion under conditions effective to polymerize and crosslink the polymerizable monomers.

A porous polymeric material prepared by such process containing the saccharide fatty acid ester surfactant and the curable high internal phase water-in-oil emulsion is also provided.

DETAILED DESCRIPTION OF THE INVENTION

It has been found that fatty acid esters of monosaccharides and oligosaccharides are effective emulsifiers for the high internal phase, water-in-oil emulsions used in the production of a low density porous crosslinked polymeric material (hereinafter "foam"). The concentrations of the saccharide fatty acid ester surfactants which are required to stabilize these emulsions are up to an order of magnitude less than the concentrations of sorbitan fatty acid ester surfactants which are typically used. Another advantage of using commercially available saccharide fatty acid ester surfactants is that little or no undesirable water-soluble sludge is formed when they are mixed with the monomers. Finally, it has been found that high internal phase, water-in-oil emulsions prepared using the saccharide fatty acid ester surfactants are stable at higher temperatures than emulsions prepared using sorbitan fatty acid ester surfactants. Use of higher temperatures permits the emulsion cure time to be significantly reduced. Reduced cure time is a significant advantage because this can lead to higher foam production rates and greater process flexibility.

In one embodiment of the inventive process, a foam is produced by first forming a curable water-in-oil high internal phase emulsion by gradually adding and mixing an aqueous solution optionally containing an electrolyte into a monomer solution (oil phase) containing a mixture of polymerizable monomers and a saccharide fatty acid ester surfactant. A polymerization initiator is also added either in the monomer solution or the aqueous solution before mixing or after formation of the emulsion depending on the desired process conditions. The curable water-in-oil high internal phase emulsion is cured (polymerized and crosslinked) by heating the emulsion at a temperature of at least about 25° C. for a time effective to cure the monomers.

The mixture of polymerizable monomers generally contains one or more vinyl monomers and a crosslinking agent. Various monomers may be used in the preparation of the foams, provided the monomers can be dispersed in or form an oil phase of a water-in-oil high internal phase emulsion (oil-soluble monomers or not water-soluble monomers) and have a polymerizable vinyl group. Suitable vinyl monomers include, for example, monoalkenyl arene monomers such as styrene, α-methylstyrene, chloromethylstyrene, vinylethylbenzene and vinyl toluene; acrylate or methacrylate esters such as 2-ethylhexyl acrylate, n-butyl acrylate, isobutyl acrylate, t-butyl acrylate, hexyl acrylate, n-butyl methacrylate, lauryl methacrylate, and isodecyl methacrylate; conjugated diolefins such as butadiene; isoprene, and piperylene; allenes such as allene, methyl allene and chloroallene; olefin halides such as vinyl chloride, vinyl fluoride and polyfluoro-olefins; and mixtures thereof.

Suitable crosslinking agents can be any multifunctional unsaturated monomers capable of reacting with the vinyl monomers. Multifunctional unsaturated crosslinking monomers include, for example, difunctional unsaturated crosslinking monomers such as divinyl benzene, diethylene glycol dimethacrylate, 1,3-butanediol dimethacrylate, and allyl methacrylate and tri-, tetra- and penta-functional unsaturated crosslinking monomers such as trimethylolpropane trimethacrylate, pentaerythritol tetramethacrylate, trimethylolpropane triacrylate, and pentaerythritol tetraacrylate, glucose pentaacrylate, glucose diethylmercaptal pentaacrylate, and sorbitan triacrylate; and poly-functional unsaturated crosslinking monomers such as polyacrylates (eg. sucrose per(meth)acrylate and cellulose (meth)acrylate). Crosslinking monomers are typically present in an amount of from about 2 weight percent to about 70 weight percent, preferably from about 5 weight percent to about 40 weight percent based on the total monomer mixture. Some of these crosslinking monomers can be incorporated as a non-crosslinked monomer as long as at least about 2 weight percent of the crosslinking monomers are crosslinked.

Suitable polymerization initiators can be water-soluble or oil-soluble. Water-soluble initiators include, for example, potassium or sodium persulfate and various redox systems such as ammonium persulfate together with sodium metabisulfite. Oil soluble (monomer soluble) catalysts include, for example, azo compounds such as azobisisobutyronitrile (AIBN); and peroxides such as benzoyl peroxide, methyl ethyl ketone peroxide, alkylperoxycarbonates such as di-2-ethylhexyl peroxydicarbonate and di(sec-butyl)peroxydicarbonate and alkylperoxycarboxylates such as t-butyl peroxyisobutyrate, 2,5-dimethyl-2,5-bis (2,3-ethylhexanoylperoxy)hexane, and t-butyl peroctoate. The preferred water-soluble polymerization initiator is potassium persulfate and the preferred oil-soluble polymerization initiators are alkylperoxycarbonates and alkylperoxycarboxylates which provide fast curing times.

Most preferably the alkylperoxycarbonates are branched at the 1-carbon position and most preferably the alkylperoxycarboxylates are branched at the α-carbon position and/or 1-carbon position. These branched alkylperoxycarbonate peroxides can be represented by the formula:

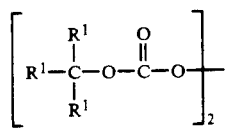

where $R^1$ is independently $C_1$ to $C_{16}$ hydrocarbons or hydrogen in which at least two of the $R'$ are hydrocarbon groups. Hydrocarbons can be alkyl, alkenyl or aryl groups. These branched alkylperoxycarboxylates can be represented by the formula:

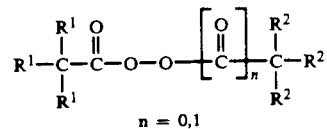

where $R^1$ and $R^2$ are independently $C^1$ to $C^{16}$ hydrocarbons or hydrogen in which at least two of the $R^1$ or $R^2$ are hydrocarbon groups. Preferably at least two of both $R^1$ and $R^2$ are hydrocarbon groups.

The water-soluble initiators and/or oil-soluble initiators should be present in an effective amount to cure (polymerize and to crosslink) the monomers. Typically the initiator can be present from about 0.005 to about 15 weight percent based on the monomers. The initiators can be introduced with the oil phase or the aqueous phase before or after formation of the high internal phase emulsion.

A water-soluble initiator such as potassium persulfate can be added to the aqueous solution before forming the emulsion or to the emulsion. An oil-soluble initiator can be added to the monomer solution or advanced monomer solution before forming the emulsion or to the emulsion. Addition of a polymerization initiator to an high internal phase water-in-oil emulsion is described in U.S. Pat. No. 5,210,104, the disclosure of which is herein incorporated by reference. The initiator added to the emulsion can optionally be blended into the emulsion by any blending technique such as, for example, using a static mixer or a pin mixer at a low shear rate, to form a curable water-in-oil high internal phase emulsion. The rate of shear must be high enough to blend the catalyst but low enough not to allow the emulsion to coalesce or liquify.

Conveniently, the initiators can be added to the oil phase (monomer phase) or aqueous phase prior to formation of the emulsion. Alternatively, at least a portion of the monomer solution can be advanced (partially polymerized) in the presence of an effective amount of an advancement initiator or by a freeradical-producing radiation source to produce an advanced monomer component prior to formation of the emulsion to reduce curing time.

As the advancement initiator any oil-soluble initiator listed above can be used. For advancing the monomer solution, the oil-soluble initiator-containing monomer solution is generally heated at a temperature within the range of above 25° C. to about 150° C. Suitable free-radical-producing radiation sources are gamma rays, electron beams, neutrons, ultra-violet or other agents capable of inducing free-radical formation. The monomers will generally be exposed to the free-radicalproducing radiation source until suitable viscosity is reached.

The advancement can be carried out on one or more or all of the monomer component(s). It is particularly advantageous to advance monomer component(s) when one or more of the monomers is volatile at the curing temperature.

When advanced, preferably the monomer mixture is advanced to a time sufficient to polymerize some monomers but not so long that the monomer mixture solidifies and no longer deforms. Typically, the monomer mixture is advanced for a time of 5% to 95%, preferably 10% to 90%, of the time necessary to form a solid (when the monomer mixture no longer deforms) or until the viscosity ratio of advanced mixture (numerator) to unadvanced, fresh mixture (denominator) is greater than 1.00, preferably within the range from about 1.03 to about 50, more preferably from about 1.07 to about 30. The time necessary to form a solid can be conveniently measured by a Solidity Test described below. The viscosity is expressed as a ratio between the viscosity of the monomer mixture and that of the advanced monomer mixture, or the viscosity of the advanced monomer mixture plus surfactant and the unadvanced mixture plus surfactant, because the absolute viscosity values are a function of temperature and whether or not the surfactant has been added to the mixture (normally addition of the surfactant raises the viscosity severalfold). Since the viscosities are generally low, it is convenient to measure them at $-78°$ C. as described below.

Additional monomers can optionally be added to the advanced monomer solution prior to emulsification to form an advanced monomer mixture. Alternatively, the advanced monomer solution can be added to a high internal phase water-in-oil emulsion containing other monomers.

Saccharide fatty acid ester surfactants can be added before or after advancement (in the oil phase) or in the monomer (oil phase) solution without advancement. When the monomer solution is advanced, the emulsion is formed with the advanced monomer solution. When less effective polymerization initiators such as benzoyl peroxide, AIBN or methyl ethyl ketone peroxide is used as an advancement initiator, additional polymerization initiator which can be an oil-soluble or a water-soluble initiator may be necessary to completely cure the foam. The additional polymerization initiator can be added in the aqueous solution or in the emulsion. The added polymerization initiator can optionally be blended into the emulsion by any blending technique such as, for example, using a static mixer or a pin mixer at a low shear rate, to form a curable water-in-oil high internal phase emulsion as described above.

The surfactant used in making the high internal phase emulsion which is to be polymerized is important in forming water-in-oil high internal phase emulsions and the final properties of the foams obtained. The saccharide fatty ester acid surfactant is typically added to the oil phase. In the inventive process, the saccharide fatty acid ester surfactant can be a monosaccharide or an oligosaccharide fatty acid ester.

Monosaccharides are polyhydroxy aldehydes or ketones having the general chemical formula $C_n(H_2O)$ where n is 3, 4, 5, 6, 7, 8, 9 or 10. Examples of monosaccharides where n is 6 are D-glucose, D-fructose, D-mannose and D-galactose. Oligosaccharides are combinations of two or more saccharides joined by 0-glucoside linkages having the general chemical formula $C_m(H_2O)$ where m is an integer from 6 to 40 and r is the number of O-glucoside linkages (or number of monosaccharide molecules that form the oligosaccharide minus one). Examples of commonly occurring disaccharides are sucrose (D-glucose plus Dfructose), lactose (D-galactose plus D-glucose), and maltose (Dglucose plus D-glucose). Each of these molecules have the general chemical formula $C_{12}(H_2O)_{11}$. Raffinose is an example of a commonly occurring trisaccharide (D-glucose plus D-fructose plus D-galactose) and has the chemical formula $C_{18}(H_2O)_{16}$.

Monosaccharides and oligosaccharides are not surfactants. However, these molecules become surfactants when they are partially esterified with fatty acids. For a typical saccharide, esterification with fatty acids preferably occurs at the methyl hydroxy side chain groups and the saccharide fatty acid esters produced can contain a mixture of esters. For example, sucrose fatty acid esters can contain a mixture of the mono-, di-, tri- esters. One method to esterifying saccharides is by transesterification between the saccharide and an ester, whereby an acyl group is transferred to saccharide in the presence of a basic catalyst, eg, potassium carbonate. The saccharide segment of a saccharide fatty acid ester is the hydrophilic or water-loving part of the molecule, while the fatty acid segments are the hydrophobic or oil-loving part of the molecule.

The preferred saccharide fatty acid ester is a fatty acid ester of a saccharide having the formula $C_n(H_2O)_{n-r}$, wherein r is an integer from 0 to 3 and $3(r+1) \leq n \leq 10(r+1)$ (n is an integer from 3 to 40, more preferably from 3 to 32). More preferably the saccharide segment of the surfactant is a monosaccharide ($r=0$), disaccharide ($r=1$), trisaccharide ($r=2$). Preferably the saccharide fatty acid esters have at least one fatty acid ester moiety having $C_8$ to $C_{22}$ hydrocarbyl segment, more $C_{18}$ hydrocarbyl segment, most preferably $C_{16}$ to $C_{18}$ hydrocarbyl segment. These hydrocarbyl segments can be alkyl (straight or branched), aryl, cyclic or arylalkyl. Preferably the hydrocarbyl segments are alkyl or arylalkyl having 12 to 18 carbon atoms. A surfactant containing one or more disaccharide fatty acid esters containing two fatty acid ester moieties (disaccharide difatty acid esters) is preferred. A surfactant containing at least one sucrose fatty acid ester, in particular, a sucrose difatty acid ester having $C_8$ to $C_{20}$ alkyl ester groups produces a particularly stable curable water-in-oil emulsion. The fatty acid esters can contain other inert substituents.

The surfactant can also contain one or more sorbitan fatty acid esters in addition to the saccharide fatty acid ester. Examples of preferable sorbitan fatty acid esters can be found in U.S. Pat. Nos. 5,200,433 and 5,210,104. For example, a combination of sucrose difatty acid ester (e.g. sucrose distearate) and a sorbitan fatty acid ester (e.g. sorbitan monolaurate) can be used as the surfactant.

Preferred monosaccharide and oligosaccharide fatty acid ester surfactants for preparing high internal phase, waterin-oil emulsions have Ester Values within the range of about 100 to about 250 mg KOH/g or, Hydroxyl Values within the range of about 100 to about 500 mg KOH/g. More preferably, the Ester Values of the saccharide fatty acid esters are within the range of about 100 to about 250 mg KOH/g and Hydroxyl Values are within the range of about 100 to about 500 mg KOH/g.

"Ester Value" is a measure of the number of ester groups contained in the sample and is defined as the difference between the Saponification Value and the Acid Value. Saponification is the base-induced hydrolysis of an ester or a free fatty acid to form a salt. The "Saponification Value" of a sample is defined as the number of milligrams of potassium hydroxide required to saponify one gram of sample. The "Acid Value" is a measure of the amount of free acids in a sample and is defined as the number of milligrams of potassium hydroxide required to neutralize the free acids in one gram of sample. Thus, the Ester Value is defined as the milligrams of potassium hydroxide per one gram of sample required to saponify the ester groups alone.

"Hydroxyl Value" is defined as number of milligrams of potassium hydroxide equivalent to the hydroxyl content of one gram of sample.

Some specific examples of commercially available saccharide fatty acid ester surfactants are Crodesta F-50 emulsifying agent (sucrose distearate from Croda Inc.) and Crodesta F-110 emulsifying agent (sucrose mono-,di-stearate from Croda Inc.). Some other preferred fatty acid esters are fatty acid esters of sucrose, fructose, galactose, glucose, lactose, maltose, mannose, arabitol, mannitol, xylitol, erythritol and raffinose such as for example, sucrose dilaurate, sucrose dioleate, sucrose dipalmitate, fructose monopalmitate, fructose dipalmitate, glucose monodecanoate, glucose monooctanoate, glucose dioctanoate, lactose dilaurate, maltose monolaurate, maltose dilaurate, mannose monodecanoate, mannose didecanoate, arabitol fatty acid esters, mannitol fatty acid esters, xylitol fatty acid esters, erythritol monooleate, mannitol monolaurate, xylitol dioleate, and the like.

Partially alkylated derivatives of the above mentioned monosaccharide and oligosaccharide fatty acid ester surfactants also exhibited excellent performance in stabilizing high internal phase, water-in-oil emulsions and are included in the definition of saccharide fatty acid ester surfactants. In the alkylated derivatives, the hydroxyl positions of the monosaccharide or oligosaccharide fatty acid ester is partially alkylated with a lower alkyl group, preferably $C_{1-6}$, more preferably $C_{1-3}$, and most preferably $C_1$ alkyl group (i.e, methylated). For example, the methylated derivatives are methylated in the hydroxyl positions of the saccharides. These alkyl saccharide fatty acid esters can be used as mixtures with non-alkylated saccharide fatty acid esters. These alkyl saccharide fatty acid esters (or saccharide ether fatty acid esters) are known, for example, in Japanese patent specification 04016194-A and Adelhorst, K. et al., Synthesis, (2), 112-15 (1990). Some specific examples of commercially available surfactants are Glucate® SS (methyl glucose sesquistearate from Amerchol Corp.), Glucate® DO (methyl glucose dioleate from Amerchol Corp.), Grillocose PS (methyl glucose stearate from R.I.T.A. Corp.) and Grillocose IS (methyl glucose isostearate from R.I.T.A. Corp.) emulsifying agents. Some other preferred alkyl saccharide fatty acid esters include ethyl glucopyranoside didodecanoate, ethyl glucopyranoside dioctadecanoate, ethyl galactopyranosyl glucopyranoside didodecanoate, ethyl galactopyranosyl glucopyranoside monododecanoate, methyl mannoside didodecanoate.

Generally, the surfactant is present in an amount effective to form a water-in-oil high internal phase emulsion (HIPE). Preferably, the saccharide fatty acid surfactant is present in the emulsion above about 0.1 weight percent, more preferably from about 0.1 weight percent to about 40 weight percent, most preferably from about 0.1 weight percent to about 12 weight percent based on the monomers. When the saccharide fatty acid surfactant is used in combination with a sorbitan fatty acid ester surfactant, the lower range can be used to obtain the beneficial effect. The saccharide fatty acid surfactant is preferably present in an amount from above about 1 weight percent based on the monomers when no additional surfactants (eg. sorbitan fatty acid esters) are present.

The relative amounts of the aqueous phase containing water and an electrolyte and monomer phase containing monomer mixtures used to form the high internal phase emulsions are a factor in determining the structural, mechanical and performance properties of the resulting polymeric foams. The ratio of water and oil in the emulsion can influence the density, cell size, and specific surface area of the foam products. To form a polymeric foam product with suitable density and high absorption capacity, the water-in-oil high internal phase emulsion (HIPE) typically contains as the internal phase, at least about 90 weight percent, based on the emulsion, of water, corresponding to a water to oil weight ratio of at least about 9:1, more preferably at least about 95 weight percent of water, most preferably at least about 97 weight percent of water, corresponding to a water to oil weight ratio of at least about 33:1.

The internal aqueous phase can preferably contain a water-soluble electrolyte to stabilize the HIPE and to make the foam more water wettable. Suitable electrolytes include inorganic salts (monovalent, divalent, trivalent or mixtures thereof), for example, alkali metal salts, alkaline earth metal salts and heavy metal salts such as halides, sulfates, carbonates, phosphates and mixtures thereof. Such electrolytes include, for example, sodium chloride, sodium sulfate, potassium chloride, potassium sulfate, lithium chloride, magnesium chloride, calcium chloride, magnesium sulfate, aluminum chloride and mixtures thereof. Mono- or di-valent salts with monovalent anions such as halides are preferred.

The formation of a water-in-oil high internal phase emulsion is dependent on a number of factors such as the monomers used, water to oil ratio, type and amount of surfactant used, mixing conditions, presence and the amount of watersoluble electrolyte. Unless all of these factors are such that it favors formation of a water-in-oil emulsion, the emulsion will form an oil-in-water emulsion rather than water-in-oil high internal phase emulsion. The formation of water-in-oil emulsions is described in U.S. Pat. Nos. 4,522,953 and 5,149,720 the disclosures of which are herein incorporated by reference.

In general, to form the water-in-oil emulsion, the water can be mixed in any way up to a water to oil ratio of about 4:1. An oil-in-water emulsion becomes preferred if the water was added all at once beyond a water to oil ratio of about 4:1. Typically, the water must be added gradually with a moderate rate of shear. A small capacity mixer such as a paint mixer with a shear rate of at least about 5 $s^{-1}$, preferably at least about 10 $s^{-1}$ can be used to mix the water-in-oil emulsion. A larger mixer equipped with an impeller with a shear rate of at least about 10 $s^{-1}$ or a pin gap mixer with a shear rate of at least about 50 $s^{-1}$, preferably at least about 100 $s^{-1}$ can also be used. If the shear rate is too low, the water-in-oil emulsion will revert to an oil-in-water emulsion. It is desirable to at least have a water to oil ratio of about 9:1, preferably at least about 19:1, more preferably at least about 30:1 for a high absorbency capacity foam.

A HIPE can be prepared in batches or continuously. To form a HIPE in batches, the emulsion is formed in a vessel or a container by gradually adding an aqueous phase in a monomer phase and/or an advanced monomer mixture under moderate rate of shear until the desired water to oil ratio is reached.

A HIPE can be prepared continuously by initially preparing a preformed emulsion of approximately the same character as the desired emulsion by the method described above, then introducing into the preformed emulsio, both the aqueous phase and monomer phase and/or advanced monomer mixture of the emulsion in such proportions so as to produce the desired emulsion. The emulsified mass is maintained in a state of continuous shear sufficient to reduce the effective viscosity of the mass near to that of the introduced phase but not above the inherent shear stability point of the desired emulsion, and then withdrawing the prepared emulsion at the desired rate.

The aqueous phase and the monomer and/or advanced monomer phase for batch process and continuous process can be introduced in a mixing vessel by an aqueous stream or a monomer stream, respectively, through one or more inlets. The streams can be combined prior to or after entering the mixing vessel then mixed in such a way to produce the desired HIPE. The mixing vessel is any container in which the high internal phase emulsion is made regardless of the type of mixer or mixer head used.

The curable water-in-oil high internal phase emulsions (curable HIPE) can be cured in a batch process or in a continuous process. The emulsion or aqueous stream or monomer stream can be heated prior to or after the addition of the catalyst.

In a batch process, the curable HIPE is collected in a suitable container with the desirable shape and cured at a temperature at least about 25° C. for a time effective to polymerize and to cure the monomers. The HIPE is preferably polymerized and cured at a temperature within the range of about 25° C. to about 90° C., as long as the emulsion is stable at the curing temperature. Alternatively, a multiple-step process as described in a U.S. Pat. No. 5,189,070 issued Feb. 23, 1993 can also be used, the disclosure of which is herein incorporated by reference. In the multi-step process the emulsion is pre-cured at a temperature of less than about 65° C. until the emulsion has a Rheometrics dynamic shear modulus of greater than about 500 pascal, (lightly gelled, having a consistency like a jelly or a gelatin referred to as "gel"), then cured at a temperature of above about 70° C. for a time effective to cure the gel. The cure can be as high as about 175° C. under suitable pressure to prevent water from boiling.

The emulsions can be heated, for example, by hot water, hot air, steam, IR, RF, microwave or ohmic heating. The HIPE should be cured until the desired properties are obtained. Typically, to obtain a cured foam, the HIPE should be cured for at least about 8 hours at 60° C or at least about 1 hour at 60° C. then 3 hours at a temperature of above about 70° C. Generally, the extent of reaction after curing is at least about 85% of the monomers, preferably at least about 90%, more preferably at least about 95% (i.e., less than about 5% of free monomers), most preferably at least about 99% (i.e., less than about 1% of free monomers) in order to obtain good properties.

These foams can be post-cured to improve the foam properties. Better properties such as, for example, increased free swell (i.e., amount of liquid a foam can initially absorb), and/or good resistance to compression deflection (i.e., retention of liquid under load) can be obtained depending on the monomer formulation by post-curing the foam at a temperature of above about 75° C., preferably greater than 90° C. by steam, hot air or other heating source. Such heating may be performed initially in a heat exchanger, oven, over heated rollers or by other means.

When the temperature is near or above the boiling point of water, pressure is preferably applied to keep the water in the liquid phase and to obtain better properties. If desired, the pressure may be lowered to boil some of the water, but in normal practice the water will be maintained in the liquid state to stabilize the monomer. The use of pressure to maintain the aqueous phase in the liquid state allows very rapid curing of emulsions at very high temperatures, provided the emulsions are stable at the high temperatures used. Pressure can be applied to the emulsion, if desired, at a pressure generally from above atmospheric pressure, typically within the range of about atmospheric pressure to about 1.03 MPa (150 psig). When the temperature is about 100° C., a pressure from about 7 to 70 kPa gauge (about 1 to 10 psig) is sufficient; when the temperature is about 130° C., a pressure from about 210 to 480 kPa gauge (about 30 psig to 70 psig) is preferred. The preferred pressures will be from just above the autogenous steam pressure of the solution to about twice that pressure on an absolute pressure basis, i.e., psia; higher or lower pressures may be used as desired to achieve specific results.

For example, the emulsion can be cured under pressure by using an autoclave operating under autogenous pressure of steam generated from pure water at a given temperature, by applying nitrogen or air pressure to prevent boiling of the emulsion or by mechanical means, such as rollers, pistons, molds, or the like.

Once the curing and/or post-curing process is completed, the water incorporated in the foam may be squeezed out, dried by heat or flashed by lowering the pressure to a suitable level to evaporate the remaining liquid to give the desired degree of dryness in the product foam. These drying techniques will preferably be used after the desired state of cure is developed in the foam material.

These foams prepared by the inventive process may be washed prior to, after or between drying stages to yield an absorbent block which is especially useful for the absorption of liquids. Typically, these foams are washed to reduce the electrolyte content of the foam with a solvent such as, for example, an alcohol, a low concentration electrolyte solution (lower concentration than the water phase) such as 1% calcium chloride solution or deionized water. The washed foams can be conveniently dried by squeezing the water and/or solvent out of the foams and air or heat drying.

The foams produced by the inventive process generally are hydrophobic and suitable for preferentially absorbing hydrophobic liquids whereas the foams produced by sorbitan esters are typically hydrophilic in character. When saccharide fatty acid ester is used as the surfactant or as a cosurfactant with a sorbitan ester the resulting foams are generally hydrophobic. The hydrophobic foams typically have a Syn-Urine (from Jayco) vertical wicking time of greater than thirty minutes, indicating little or no Syn-Urine penetration into the foam. In comparison, foams prepared using sorbitan monolaurate emulsifier alone generally have a Syn-Urine vertical wicking time of less than ten minutes. Decane vertical wicking time for the hydrophobic foams are generally less than five minutes, indicating that these foams preferentially absorb non-aqueous liquids.

Another measure of relative hydrophobicity/hydrophilicity is the absorbency ratio of SynUrine vertical wicking time ("VWT") to decane vertical wicking time ("DVWT"). Hydrophilic foams generally have values of VWT/DVWT less than ten while hydrophobic foams generally have values greater than ten, more preferably greater than fifteen, most preferably greater than about twenty. The foams produced by the inventive process are also generally non water-swellable unless chemically modified.

The foams produced by the inventive process using saccharide fatty acid ester emulsifiers generally have a smaller cell size than foams reduced using sorbitan fatty acid ester emulsifiers. These foams generally have a dry density of less than about 0.1 g/cc. The porous crosslinked vinyl polymeric foam materials formed by the inventive process have at least one saccharide fatty acid ester incorporated therein. The location of the saccharide fatty acid ester incorporated within the foam is not known. However, the saccharide fatty acid ester can be physically incorporated or held, on the surface or interior of the foam, in the pores or within the struts of the foam homogeneously distributed or separately clustered. The term saccharide fatty acid ester includes decomposition residue of the saccharide fatty acid esters including the residual fatty acid ester segments and the residual saccharides.

ILLUSTRATIVE EMBODIMENT

The following illustrative embodiments describe the process of the invention and are provided for illustrative purposes and are not meant as limiting the invention.

Examples 1-9 demonstrate the process of the invention using saccharide fatty acid ester surfactants as the surfactant for the high internal phase water-in-oil emulsion. Examples 10 and 11 demonstrate the process of the invention using mixtures of saccharide fatty acid ester surfactants and a sorbitan fatty acid ester surfactant for the high internal phase water-in-oil emulsions. Sorbitan fatty acid ester surfactants were used as comparison in comparative examples 1-4. Saccharide fatty acid esters, alone or as cosurfactants with sorbitan fatty acids, are effective water-in-oil emulsifiers at lower concentrations and higher use temperatures than sorbitan fatty acid ester surfactants. Foams made using saccharide fatty acid esters as the surfactant are hydrophobic (preferentially absorbing hydrophobic liquids), and generally have a smaller cell size than foams made with sorbitan fatty acid ester surfactants. Table 1 summarizes the experimental results.

Examples 12 and 13 demonstrate that commercially available saccharide fatty acid ester surfactants form little or no water soluble sludge when they are mixed with the monomer phase. Table 2 summarizes the experimental results.

TESTING METHODS

Hydroxyl value

ASTM method E 222, test method B (reflux method) is used except 4:1 by volume pyridine:acetic anhydride reagent is used instead of 1000:105 by volume reagent and the sample is refluxed for 20 minutes in 10 mL of the reagent. Condenser is rinsed with 10 mL of water and then 50 mL of 99% isopropanol instead of water. 0.5N potassium hydroxide solution is used instead of the 0.5N sodium hydroxide solution for titration.

Saponification Value

ASTM method D 94 is used except as follows. The sample is used neat instead of dissolving in methyl ethyl ketone and 0.6N ethanolic potassium hydroxide solution is used instead of 0.5N solution. The sample is refluxed for 1.5 hours instead of 30 minutes and instead of naphtha, 1:1 by volume isopropanol/diethyl ether solution is added.

Acid Value

ASTM method D 1613 is used except as follows. The sample is dissolved in an appropriate neutralized solvent, preferably a 1:1 volume mixture of ethanol:toluene, instead of water or isopropyl alcohol. 0.1N ethanolic potassium hydroxide solution is used instead of the 0.05N sodium hydroxide solution for titration.

Ester value

Ester value is calculated by subtracting the acid value from the saponification value obtained above.

Vertical Wicking Time ("VWT")

From a foam slice, cut at 0.35 inches (0.89 cm) thickness, a 1 to 2 cm wide strip is cut, greater than 5 cm in length. The strip of foam is clamped or taped to a metal ruler, with the bottom of the foam strip flush with the 0 mark on the ruler. The ruler and foam are placed in a container of approximately 100 ml Syn-Urine from Jayco, in an incubator at 99° F. (37° C.) so the bottom of the strip (0 mark) is barely touching the surface of the Syn-Urine (less than 1 mm). The SynUrine is dyed with food coloring to more easily monitor its absorption and rise in the foam. A stopwatch is used to measure the time required for the liquid level to reach 5 cm vertical height in the foam sample.

Decane Vertical Wicking Time ("DVWT")

From a foam slice, cut at 0.35 inches (0.89 cm) thickness, a 1 to 2 cm wide strip is cut, greater than 5 cm in length. The strip of foam is clamped or taped to a metal ruler, with the bottom of the foam strip flush with the 0 mark on the ruler. The ruler and foam are placed in a container of approximately 100 ml decane, in an incubator at 99° F. (37° C.) so the bottom of the strip (0 mark) is barely touching the surface of the decane (less than 1 mm). The decane is dyed with food coloring to more easily monitor its absorption and rise in the foam. A stopwatch is used to measure the time required for the liquid level to reach 5 cm vertical height in the foam sample.

Solidity Test

A flat-tipped probe of about 6 mm diameter is placed on top of an advanced monomer mixture to create a pressure at the flat-tip of about 2.1 kPa (0.3 psi). The ease and penetration of the object into the gel was measured. The monomer mixture is considered solid when the object no longer penetrates or penetrates less than about 1 mm.

Viscosity

At selected times, aliquots of approx. 5 ml are removed and placed in 8 dram vials. If the aliquots are above ambient temperature, the aliquots are then quickly cooled in wet ice to ambient temperature (approx. 24° C). The aliquots are chilled in acetone/dry ice slush bath for approx. 10 minutes to a temperature of approx. −78° C. The warm aliquots may be chilled immediately to approx. −78° C. While the aliquots are kept cold, the viscosity is run using Brookfield Viscometer, Model RVTD equipped with a #6 Spindle (manufactured by Brookfield Engineering Lab, Stoughton, Mass.).

COMPARATIVE EXAMPLE 1

2 milliliters (ml) of styrene, 2 ml of divinylbenzene (commercial divinyl benzene containing 55% divinylbenzene from Aldrich Chemical Co.), 6 ml of 2-ethylhexylacrylate, and 1.06 grams (g) of SPAN ® 20 emulsifying agent (sorbitan monolaurate from Fluka Chemical Corp. or Aldrich Chemical Co.) were mixed together and heated to 40° C. The proportions correspond to 12 parts of SPAN ® 20 per 100 parts of monomer on a weight basis (12 phr). 10 ml of the solution was then transferred to a 500 ml beaker submersed in a 45° C. water bath. A double bladed paint stirrer was positioned into the beaker and the speed was adjusted to 300 revolutions per minute (rpm). An aqueous solution containing 10% by weight calcium chloride and 0.15% by weight potassium persulfate was prepared. 300 ml of the aqueous solution was heated to 40° C. and added dropwise into the beaker over a 30 minute period to form a high internal phase water-in-oil emulsion. The emulsion had a creamy white appearance.

Foams were prepared by transferring the emulsion to a sealed plastic container and placing the container in an oven at 70° C. for 24 hours. After this time period the container was taken out of the oven and the amount of free water in the container was measured. The quantity reported in Table 1 is the percentage of the initial amount of aqueous phase used to prepare the emulsion. The percent free water indicates the amount of emulsion breakage and/or foam shrinkage by the time curing of the material was stopped. Smaller percentages of free water are obtained for more effective emulsifiers and correspond to better foam properties.

Vertical Wicking Time ("VWT") and Decane Vertical Wicking Time ("DVWT") measurements were made as described above. The results are shown in Table 1.

COMPARATIVE EXAMPLE 2

The procedure of Comparative Example 1 was repeated except that the emulsion was prepared at 60° C. rather than 40° C. Table 1 indicates that a slightly larger amount of free water was obtained at this higher temperature.

COMPARATIVE EXAMPLE 3

The procedure of Comparative Example 1 was repeated except that the emulsion was prepared at 80° C. rather than 40° C. Table 1 indicates that SPAN ® 20 emulsifying agent was not effective in stabilizing high internal phase, water-in-oil emulsions at this temperature.

COMPARATIVE EXAMPLE 4

The procedure of Comparative Example 1 was repeated except that 0.53 g of SPAN ® 20 emulsifying agent (6 phr) was used. Table 1 indicates that SPAN ® 20 emulsifying agent could not stabilize a high internal phase, water-in-oil emulsion at this surfactant concentration.

EXAMPLE 1

The procedure of Comparative Example 1 was repeated except that 0.27 g (3 phr) of CRODESTA F50 emulsifying agent was used in place of the SPAN ® 20 emulsifying agent. Table indicates that this surfactant concentration was effective in stabilizing a high internal phase emulsion which could be cured into a foam.

EXAMPLE 2

The procedure of Comparative Example 1 was repeated except that 0.27 g (3 phr) of CRODESTA F50 emulsifying agent was used in place of the SPAN ® 20 emulsifying agent and the emulsion was prepared at 70° C. instead of 40° C. Table 1 indicates that CRODESTA F50 emulsifying agent was effective in stabilizing a high internal phase emulsion which could be cured into a foam at this concentration and emulsion temperature.

EXAMPLE 3

The procedure of Comparative Example 1 was repeated except that 0.09 g (1 phr) of CRODESTA F50 emulsifying agent was used in place of the SPAN ® 20 emulsifying agent and the emulsion was prepared at 70° C. instead of 40° C. Table 1 indicates that CRODESTA F50 emulsifying agent was effective in stabilizing a high internal phase emulsion which could be cured into a foam at this concentration and emulsion temperature.

EXAMPLE 4

The procedure of Comparative Example 1 was repeated except that 0.27 g (3 phr) of CRODESTA F110 emulsifying agent was used in place of the SPAN ®20 emulsifying agent and the emulsion was prepared at 80° C. instead of 40° C. Table 1 indicates that CRODESTA F50 emulsifying agent was effective in stabilizing a high internal phase emulsion which could be cured into a foam at this concentration and emulsion temperature.

EXAMPLE 5

The procedure of Comparative Example 1 was repeated except that 0.53 g (6 phr) of CRODESTA F10 emulsifying agent was used in place of the SPAN ® 20 emulsifying agent and the emulsion was prepared at 80° C. instead of 40° C. Table 1 indicates that CRODESTA F50 emulsifying agent was effective in stabilizing a high internal phase emulsion which could be cured into a foam at this concentration and emulsion temperature.

EXAMPLE 6

The procedure of Comparative Example 1 was repeated except that 0.27 g (3 phr) of GLUCATE ® SS emulsifying agent was used in place of the SPAN ® 20 eemulsifying agent. Table 1 indicates that this surfactant concentration was effective in stabilizing a high internal phase emulsion which could be cured into a foam.

EXAMPLE 7

The procedure of Comparative Example 1 was repeated except that 1.06 g (12 phr) of GLUCATE ® DO emulsifying agent was used in place of the SPAN ® 20 emulsifying agent. Table 1 indicates that GLUCATE ® DO emulsifying agent was effective in stabilizing a high internal phase emulsion which could be cured into a foam.

EXAMPLE 8

The procedure of Comparative Example 1 was repeated except that 1.06 g (12 phr) of GRILLOCOSE PS emulsifying agent was used in place of the SPAN® emulsifying agent. Table 1 indicates that GRILLOCOSE PS emulsifying agent was effective in stabilizing a high internal phase emulsion which could be cured into a foam.

EXAMPLE 9

The procedure of Comparative Example 1 was repeated except that 1.06 g (12 phr) of GRILLOCOSE IS emulsifying agent was used in place of the SPAN® 20 emulsifying agent and the emulsion was prepared at 60° C. instead of 40° C. Table 1 indicates that GRILLOCOSE IS emulsifying agent was effective in stabilizing a high internal phase emulsion which could be cured into a foam.

EXAMPLE 10

The procedure of Comparative Example 1 was repeated except that 0.53 g (6 phr) of SPAN® 20 emulsifying agent and 0.09 g (1 phr) of CRODESTA F50 emulsifying agents were used in place of the SPAN® 20 emulsifying agent alone. Table 1 indicates that the combination of emulsifying agents was effective in stabilizing a high internal phase emulsion which could be cured into a foam. Thus, use of CRODESTA F50 as a coemulsifier with SPAN® 20 reduces the overall concentration of emulsifier required to produce a foam.

EXAMPLE 11

The procedure of Comparative Example 1 was repeated except that 0.14 g (2 phr) of SPAN® 20 emulsifying agent and 0.09 g (1 phr) of CRODESTA F50 emulsifying agents were used in place of the SPAN® 20 emulsifying agent alone. Table 1 indicates that the combination of emulsifying agents was effective in stabilizing a high internal phase emulsion which could be cured into a foam. Thus, use of CRODESTA F50 as a coemulsifier with SPAN® 20 reduces the overall concentration of emulsifier required to produce a foam.

EXAMPLE 12

Five jars were prepared, each containing 10 ml of styrene, 10 ml of divinylbenzene, 30 ml of 2-ethylhexylacrylate, and 6 g of surfactant. The surfactants used were SPAN® 20, CRODESTA F50, CRODESTA F10, GLUCATE® DO, and GRILLOCOSE PS emulsifying agents. (Only 2 g of Grillocose PS was added to one of the sample jars.) The five jars were placed in a water bath at 50° C. and mixed intermittently for 30 minutes. After removing the jars from the water bath they were placed in an oven overnight at 50° C., to allow any sludge from the surfactants to settle out. The jars were then decanted away from the sludge. Excess solvent remaining in the jars was removed by placing the jars in a vacuum oven at 60° C. for 8 hours. The weight of sludge in each of the jars was then measured. Table 2 summarizes the experimental results. The amount of sludge which settled out in each jar is expressed as a weight percent of the original amount of surfactant added to the jar. It was found that the sorbitan fatty acid ester surfactant formed a sludge layer, while little or no sludge was measured for the saccharide fatty acid ester surfactants.

EXAMPLE 13

Two jars were prepared, each containing 10 ml of styrene, 10 ml of divinylbenzene, 30 ml of 2-ethylhexylacrylate, and 6 g of surfactant. The surfactants used were SPAN® 20 and CRODESTA F110 emulsifying agents. The two jars were placed in a water bath at 80° C. and mixed intermittently for 30 minutes. After mixing the jars were kept in the water bath for 6 hours at 80° C. to allow any sludge from the surfactants to settle out. The jars were then decanted away from the sludge. Excess solvent remaining in the jars were removed by placing the jars in a vacuum oven overnight at 60° C. The weight of sludge in each of the jars were then measured. Table 2 summarizes the experimental results. The amount of sludge which settled out in each jar is expressed as a weight percent of the original amount of surfactant added to the jar. It was found that CRODESTA F110 emulsifying agent formed a much smaller sludge layer than SPAN® 20 emulsifying agent.

TABLE 2

| SURFACTANT | % w SLUDGE | |
|---|---|---|
| | EXAMPLE 12 | EXAMPLE 13 |
| SPAN® 20 | 6.2 | 6.3 |
| CRODESTA F50 | 0 | — |
| CRODESTA F110 | — | 1.1 |
| CRODESTA F10 | 0 | — |
| GLUCATE® DO | 0 | — |
| GRILLOCOSE PS | 1.5 | — |

TABLE 1

| Ex. | Surfactant Name | phr | w/o Ratio (by vol) | Emulsion Temp °C. | % Free Water (basis total water) | Vertical Wicking, seconds VWT | DVWT | VWT/DVWT |
|---|---|---|---|---|---|---|---|---|
| 1C | SPAN® 20 | 12 | 30/1 | 40 | 0.7 | 398 | 150 | 2.7 |
| 2C | SPAN® 20 | 12 | 30/1 | 60 | 2.0 | — | — | — |
| 3C | SPAN® 20 | 12 | 30/1 | 80 | >75 | — | — | — |
| 4C | SPAN® 20 | 6 | 30/1 | 40 | >75 | — | — | — |
| 1 | CRODESTA F50 | 3 | 30/1 | 40 | 3.7 | >1800 | 68 | >26.5 |
| 2 | CRODESTA F50 | 3 | 30/1 | 70 | 0 | — | — | — |
| 3 | CRODESTA F50 | 1 | 20/1 | 70 | 2.7 | — | — | — |
| 4 | CRODESTA F110 | 3 | 30/1 | 80 | 1.3 | >1800 | 83 | >21.7 |
| 5 | CRODESTA F10 | 6 | 30/1 | 80 | 5.3 | — | — | — |
| 6 | GLUCATE® SS | 3 | 30/1 | 40 | 0 | >1800 | 64 | >28.1 |
| 7 | GLUCATE® DO | 12 | 30/1 | 40 | 0 | >1800 | 43 | >41.9 |
| 8 | GRILLOCOSE PS | 12 | 30/1 | 40 | 1.7 | >1800 | 66 | >27.3 |
| 9 | GRILLOCOSE IS | 12 | 30/1 | 60 | 2.3 | — | — | — |
| 10 | SPAN® 20/ CRODESTA F50 | 6/1 | 30/1 | 40 | 1.3 | >1800 | 67 | >26.9 |
| 11 | SPAN® 20/ CRODESTA F50 | 2/1 | 30/1 | 40 | 0.7 | >1800 | 43 | >41.9 |

We claim:

1. A process for the production of a porous crosslinked polymeric material comprising the steps of:
   (a) providing a water-in-oil emulsion comprising (i) a mixture of polymerizable monomers comprising at least one vinyl monomer and from about 2 to about 70 weight percent, based on the mixture, of a multifunctional unsaturated crosslinking monomer, (ii) at least 90 weight percent, based on the emulsion, of water as the internal phase, (iii) an effective amount of a surfactant comprising at least one saccharide fatty acid ester to produce the water-in-oil emulsion, and (iv) an effective amount of at least one polymerization initiator to polymerize and crosslink the polymerizable monomers;
   (b) heating the water-in-oil emulsion under conditions effective to polymerize and crosslink the polymerizable monomers; and
   (c) removing at least a portion of the water in said crosslinked emulsion.

2. The process of claim 1 wherein the saccharide fatty acid ester is a fatty acid ester of a saccharide having the formula $C_n(H_2O)_{n-r}$, wherein r is an integer from 0 to 3 and $3(r+1) \leq n \leq 10(r+1)$.

3. The process of claim 2 wherein the saccharide fatty acid ester is partially alkylated in the hydroxyl positions of the saccharides.

4. The process of claim 2 wherein the saccharide fatty acid ester has at least one fatty acid ester moiety having $C_8$ to $C_{22}$ hydrocarbyl segment.

5. The process of claim 4 wherein the saccharide fatty acid ester has an ester value within the range of about 100 mg to 250mg KOH/g or hydroxyl value within the range of about 100 to about 500 mg KOH/g.

6. The process of claim 5 wherein the saccharide fatty acid ester has at least one fatty acid ester moiety having $C_{12}$ to $C_{20}$ hydrocarbyl segment.

7. The process of claim 5 wherein the saccharide fatty acid ester has an ester value within the range of about 100 mg to 250 mg KOH/g and hydroxyl value within the range of about 100 to about 500 mg KOH/g.

8. The process of claim 4 wherein the saccharide fatty acid ester is selected from the group consisting of fatty acid esters of sucrose, fructose, galactose, glucose, lactose, maltose, mannose, arabitol, mannitol, xylitol, erythritol and raffinose.

9. The process of claim 4 in which the vinyl monomer is selected from the group consisting of monoalkenyl arenes arylate or methacrylate esters, conjugatred diolefins, allenses, olefin halides, and mixtures thereof.

10. The process of claim 9 in which the multifunctional unsaturated crosslinking monomer is selected from the group consisting of divinyl benzene, diethlene glycol dimethacrylate, 1,3-butanediol dimethacrylate, allyl methacrylate, trimethylolpropane trimethacrylate, pentaerythritol tetramethacrylate, trimethylolpropane triacrylate, pentaerythritol tetraacrylate, glucose pentaacrylate, glucose diethylmercaptal pentaacrylate, sorbitan triacrylate, sucrose per(meth)acrylate, and cellulose (meth)acrylate.

11. The process of claim 9 in which the water-in-oil emulsion comprises as the internal phase, at lest about 95 weight percent, based on the emulsion, of water.

12. The process of claim 1 in which the surfactant is present in an amount from about 0.1 to about 40 weight percent based on the polymerizable monomers.

13. The process of claim 1 in which the surfactant further comprises at least one sorbitan fatty acid ester.

* * * * *